United States Patent
Vija et al.

(10) Patent No.: US 7,928,727 B2
(45) Date of Patent: Apr. 19, 2011

(54) ADAPTING ACQUISITION TIME IN NUCLEAR IMAGING

(75) Inventors: Alexander Hans Vija, Evanston, IL (US); Amos Yahil, Stony Brook, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 212 days.

(21) Appl. No.: 12/478,295

(22) Filed: Jun. 4, 2009

(65) Prior Publication Data

US 2010/0308817 A1 Dec. 9, 2010

(51) Int. Cl.
*G11V 3/00* (2006.01)
(52) U.S. Cl. ........................................ 324/300; 324/309
(58) Field of Classification Search .......... 324/300–322; 600/407–445; 382/130, 131; 250/370
See application file for complete search history.

(56) References Cited

U.S. PATENT DOCUMENTS

| | | | |
|---|---|---|---|
| 7,180,074 B1 * | 2/2007 | Crosetto | 250/370.09 |
| 7,519,412 B2 * | 4/2009 | Mistretta | 600/407 |
| 7,881,510 B2 * | 2/2011 | Doyle | 382/128 |
| 2006/0284095 A1 * | 12/2006 | Muehllehner et al. | 250/363.02 |
| 2009/0161933 A1 * | 6/2009 | Chen | 382/131 |
| 2009/0175523 A1 * | 7/2009 | Chen et al. | 382/130 |
| 2009/0262996 A1 * | 10/2009 | Samsonov et al. | 382/130 |
| 2010/0308228 A1 * | 12/2010 | Vija et al. | 250/363.04 |

* cited by examiner

*Primary Examiner* — Brij B Shrivastav
(74) *Attorney, Agent, or Firm* — Peter L. Kendall

(57) ABSTRACT

Methods of determining an acquisition time adapted to a region of interest for a nuclear imaging process of a patient include detecting radiation from at least a first viewing angle during a first test amount of time, generating first test data from the detected radiation, reconstructing a nuclear event distribution from the first test data, determining a test signal-to-noise ratio for the reconstructed nuclear event distribution within the region of interest, and determining the acquisition time using the test signal-to-noise ratio and the first test amount of time.

20 Claims, 5 Drawing Sheets

ADAPTING ACQUISITION TIME IN NUCLEAR IMAGING

TECHNICAL FIELD

The invention relates to nuclear imaging in medicine, and in particular, to adapting acquisition time in nuclear imaging.

BACKGROUND

In nuclear imaging, one administers a radioactive substance, usually a disease specific biomarker, to a patient and detects emitted radiation with a detector system. Examples of nuclear imaging techniques includes planar nuclear imaging and tomographic nuclear imaging. Planar imaging is performed with a stationary imaging detector (e.g., a flat panel detector for planar scintigraphy) that detects primarily radiation emitted towards one direction, while tomograpic imaging is performed with detector systems that detect radiation emitted into a plurality of directions. Examples of tomographic nuclear imaging include, for example, single photon emission computed tomography (SPECT) and positron emission tomography (PET). SPECT can be performed with one or several detectors (e.g., gamma cameras) that can be positioned or rotated around the patient, while PET is usually performed with a stationary imaging detector covering opposite sides of the patient (e.g., a ring detector).

For a nuclear event, the detector systems can detect, for example, the location of the respective detector pixel, the time of detection, and/or the energy of radiation emitted by nuclear events. The detected information (also referred to as nuclear data) is used to reconstruct an image of the distribution of the administered radioactive substance within the patient.

An overview of SPECT and PET systems and iterative image reconstruction for emission tomography is given in chapter 7 and chapter 21 of M. Wernick and J. Aarsvold, "Emission tomography: the fundamentals of PET and SPECT," Elsevier Academic Press, 2004, the contents of which are herein incorporated by reference. An overview of different reconstruction methods is given in R. C. Puetter et al., "Digital Image Reconstruction: Deblurring and Denoising," Annu. Rev. Astro. Astrophys., 2005, 43: 139-194, the contents of which are herein incorporated by reference.

SUMMARY

The invention is based in part on the recognition that in nuclear imaging, one can adapt the acquisition time according to a selected region of interest (ROI). The adaptation can be based on the evaluation of the signal-to-noise ratio within the ROI, which is herein referred to as the footprint signal-to-noise ratio (FSNR).

The acquisition time is an amount of time during which nuclear data is acquired. For example, the acquisition time can be a minimum acquisition time, i.e., the total amount of time during which nuclear events should at least be recorded so that the recorded nuclear data result in an image with a desired FSNR. Another example of an acquisition time that can be adapted is the so called dwell time, i.e., the amount of time for detecting radiation emitted in a specific viewing angle, wherein a viewing angle usually corresponds to an angular position of a detector, and the detector may be configured to detect radiation in a range around a particular angle as determined, for example, by the configuration of the detector's collimator.

For so called "point and stare" SPECT imaging, each detector position is associated with a dwell time. For rotating systems, the dwell time can be adjusted by the angular rotation speed of the detector. By analyzing the contributions of the various viewing angles to the FSNR, one can adapt the dwell times such that the recorded nuclear data result in a desired FSNR. Moreover, one can analyzing the contributions of the various viewing angles to the FSNR to see whether specific viewing angles can be neglected during the nuclear imaging examination.

In general, in one aspect, the invention features methods of determining an acquisition time adapted to a region of interest for a nuclear imaging process of a patient that include detecting radiation from at least a first viewing angle during a first test amount of time, generating first test data from the detected radiation, reconstructing a nuclear event distribution from the first test data, determining a test signal-to-noise ratio for the reconstructed nuclear event distribution within the region of interest, and determining the acquisition time using the test signal-to-noise ratio and the first test amount of time.

Embodiments of the methods can include one or more of the following features and/or features of other aspects.

The methods can further include using the acquisition time as a control parameter for controlling the nuclear imaging process. In some embodiments, the methods can further include controlling the nuclear imaging process to acquire nuclear data during an amount of time at least as long as the acquisition time. The acquired nuclear data can include the first test data.

The methods can further include reconstructing a nuclear image from the acquired nuclear data.

In some embodiments, the acquisition time can be a dwell time associated with the detection of radiation from the first viewing angle, and wherein the method further comprises controlling the nuclear imaging process to acquire nuclear data from the first viewing angle during an amount of time at least as long as the dwell time. The acquired nuclear data can include the first test data. In some embodiments, controlling the nuclear imaging process to acquire nuclear data from the first viewing angle can include controlling the speed of rotation of a detector to control an amount of time during which a detector can detect radiation emitted from the first viewing angle. In some embodiments, controlling the nuclear imaging process to acquire nuclear data from the first viewing angle can include controlling an amount of time during which a detector is in a stationary position for detecting radiation from the first viewing angle.

In certain embodiments, detecting radiation from at least a first viewing angle can include detecting radiation with a plurality of detector pixels of a detector.

Determining the test signal-to-noise ratio can include determining a count rate from the first test data and the first test amount of time and determining pixel weights associated with the detector pixels and the region of interest.

The methods can further include detecting radiation from at least in one additional viewing angle, and wherein determining the test signal-to-noise ratio for the region of interest includes determining count rates for the first viewing angle and the at least one additional viewing angle. Determining the acquisition time can include determining dwell times for the first viewing angle and the at least one additional viewing angle by optimizing a merit function for the dwell times. The merit function can be a function of at least one of a count rate for the first viewing angle, a count rate for the at least one additional viewing angle, and pixel weights associated with at least one of pixels of a detector system, the region of interest, the first viewing angle, and the at least one additional viewing angle.

The methods can further include providing a desired signal-to-noise ratio for the region of interest, and wherein determining the acquisition time includes determining that the test signal-to-noise ratio is at least as large as the desired signal-to-noise ratio.

In general, in a further aspect, the invention features nuclear imaging apparatuses that include a detector system configured to detect radiation during a nuclear imaging process from at least one viewing angle and to derive test data from the radiation, and a control and reconstruction unit configured to determine a test signal-to-noise ratio for a region of interest from the test data, and, based on the test signal-to-noise ratio, to control the amount of time of the nuclear imaging process during which the detector system is configured to detect radiation.

In some embodiments, the detector system can includes at least one of a planar nuclear imaging detector, a SPECT detector, and a PET detector.

The amount of time can be a minimum acquisition time of the nuclear imaging process.

In some embodiments, the amount of time can be a dwell time of a SPECT imaging process for the at least one viewing angle.

In general, in a further aspect, the invention features computer-readable mediums having encoded thereon software for controlling a nuclear imaging system, the software including instructions for detecting radiation from at least a first viewing angle during a first amount of time, generating first test data from the detected radiation, reconstructing a nuclear event distribution from the first test data, determining a test signal-to-noise ratio for the reconstructed nuclear event distribution within the region of interest, and determining the acquisition time using the test signal-to-noise ratio and the first time interval.

Embodiments of the nuclear imaging apparatuses and computer-readable mediums can also include one or more of the features of other aspects.

In some implementations, the proposed methods and systems can lead to greater efficiency in clinical nuclear medicine.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like reference symbols in the various drawings indicate like elements.

DETAILED DESCRIPTION

Medical imaging techniques in nuclear medicine produce two-, three-, or four-dimensional images or maps of, for example, functional processes in a patient's body by using nuclear properties of matter. For some types of nuclear imaging, one administers a radioactive substance to the patient and detects emitted radiation with a detector system. The detector system provides the recorded nuclear data to a control and reconstruction unit. Examples of detector system include a ring detector for PET and one or several gamma cameras for planar nuclear imaging and SPECT, respectively. Then, using especially adapted reconstruction algorithms, the control and reconstruction unit reconstructs an image from the nuclear data.

Because too much radiation can be harmful to the patient, the amount of the administered radioactive substance and therefore the flux of detected nuclear radiation, i.e. the number of counts per unit time, is limited. As a result, in nuclear imaging one often has to reconstruct the image using only a limited number of counts acquired during a limited amount of time.

The inventors realized that one can use the available amount of acquisition time more effectively by observing statistical features of the image (e.g., the footprint signal-to-noise ratio (FSNR) in a region of interest (ROI)). By doing so, one can avoid or at least reduce the radiation-inflicted harm to the patient.

In some embodiments, one can reduce the amount of time required for a single image and thus acquire more images during a single administration of a radioactive substance. In some embodiments, one can increase the quality of an image reconstructed from nuclear data acquired in a predefined available amount of acquisition time.

Figure 1:
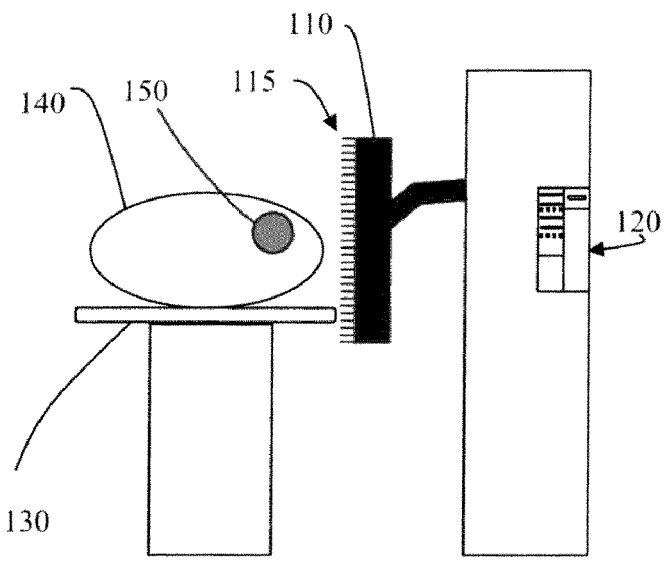
FIG. 1 is a schematic view of a planar nuclear system.
Figure 2:
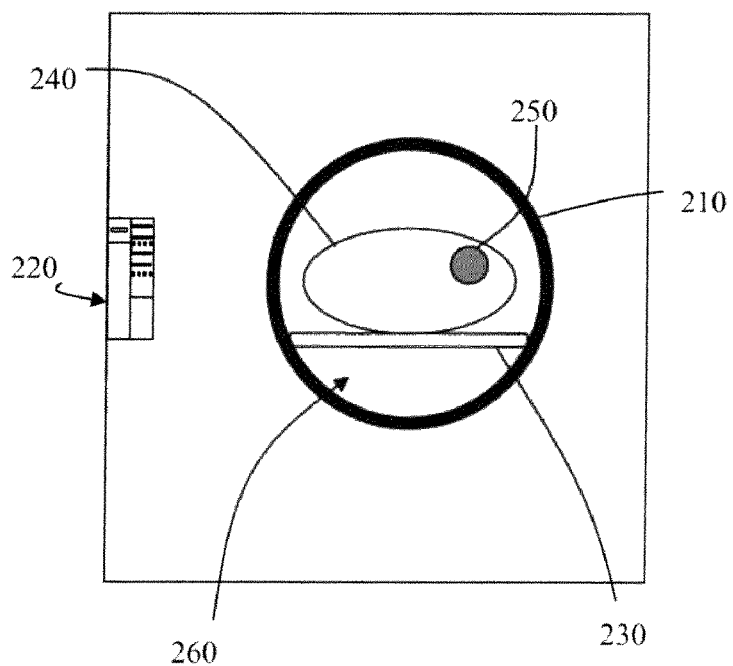
FIG. 2 is a schematic view of a PET system.
Figure 3:
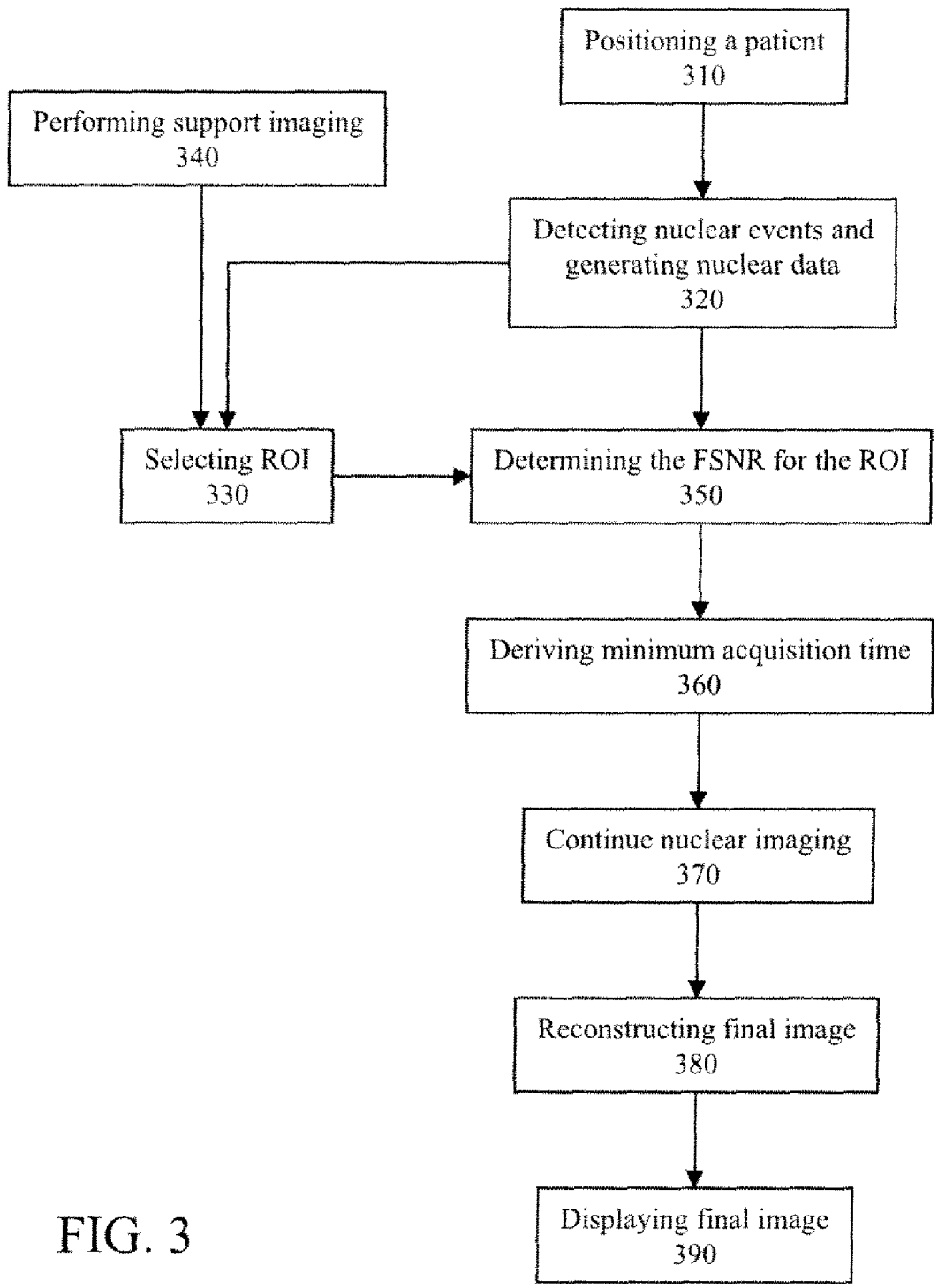
FIG. 3 is an example of a flow chart illustrating adaptation of a minimum acquisition time.

In connection with FIGS. 1-3, various nuclear imaging systems and their operation are described as examples of nuclear imaging systems that can be used for adapting a nuclear imaging process based on the FSNR of a ROI.

FIG. 1 shows a planar system 100 with an imaging detector 110, a control and reconstruction unit 120, and a patient table 130. Imaging detector 110 can be positioned relative to a patient 140 to observe a ROI 150. In FIG. 1, for example, imaging detector 110 is positioned at the side of patient 140 that is close to ROI 150. Imaging detector 110 can be, for example, a planar γ-detector with a focusing collimator system 115.

During operation, imaging detector 110 detects γ-radiation emitted from a radioactive substance administered to patient 140 and provides the resulting nuclear data to control and reconstruction unit 120.

FIG. 2 shows a PET system 200 with a stationary ring detector system 210. Ring detector system 210 provides an opening 260 for receiving a patient 240 positioned on a support table 230. Ring detector system 210 is configured to simultaneously detect γ-radiation (in particular, pairs of photons) that is emitted in opposing directions from an annihilation event occurring within patient 240. The detected nuclear data is provided to a control and reconstruction unit 220 for analysis and reconstruction.

FIG. 3 shows an example flowchart 300 of a nuclear imaging process that uses FSNR analysis to determine a minimum acquisition time, i.e., a minimal amount of time during which nuclear data should be acquired. First, a patient is positioned on a support table and the radioactive substance is administered (step 310). Then, while the patient stays stationary on the support table, radioactive decay of the administered substance cause the emission of radiation that is detected with nuclear imaging detectors and used to generate nuclear data to be provided to a control and reconstruction unit (step 320).

One then reconstructs a rough nuclear image from the nuclear data and selects a ROI (step 330). The quality of the nuclear image should allow distinguishing a ROI from a surrounding region that is not of interest. The nuclear data can be the first nuclear data of longer nuclear imaging process, or it can be nuclear data that originates from a pre-imaging process. Alternatively, a user can select the ROI based on an image derived from a separate imaging process (step 340). For example, one can select the ROI based on a previously generated CT. In the latter case, the separately detected image needs to be registered in space to the field-of-view of the nuclear imaging process.

Then, one determines a FSNR for the selected ROI (step 350) and derives from that FSNR a minimum acquisition time (step 360). The minimum acquisition time is expected to allow reconstruction of a nuclear image within a predefined FSNR.

The determination of the minimum acquisition time can include comparing an associated FSNR with a desired FSNR and/or performing an optimization process of the minimum acquisition time for improving the FSNR. Similar to image reconstruction, the determination of the minimum acquisition time can use a system matrix that describes the performed imaging process for e.g., planar or volumetric reconstruction the nuclear image.

The nuclear imaging process can then be continued or restarted so that nuclear data can be acquired for at least an amount of time that is as long as the minimum acquisition time (step 370).

Based on the acquired nuclear data, one then reconstructs final image (step 380). This reconstruction can involve the system matrix and use iteratively improved data modeling. The final image can, for example, be displayed on a display (step 390) or provided to a diagnostic analysis tool.

While FIGS. 1 and 2 refer to planar imaging and PET imaging, SPECT imaging can also profit from determining a minimum acquisition time. An example of a SPECT system 400 is described in connection with FIG. 4.

However, the signal-to-noise ratio for the detection process carried out by the stationary detectors of planar imaging and PET imaging depends on the available acquisition time. The signal-to-noise ratio for SPECT imaging additionally depends on the amount of time that is available to detect radiation in specific viewing angles (dwell time).

Figure 4:
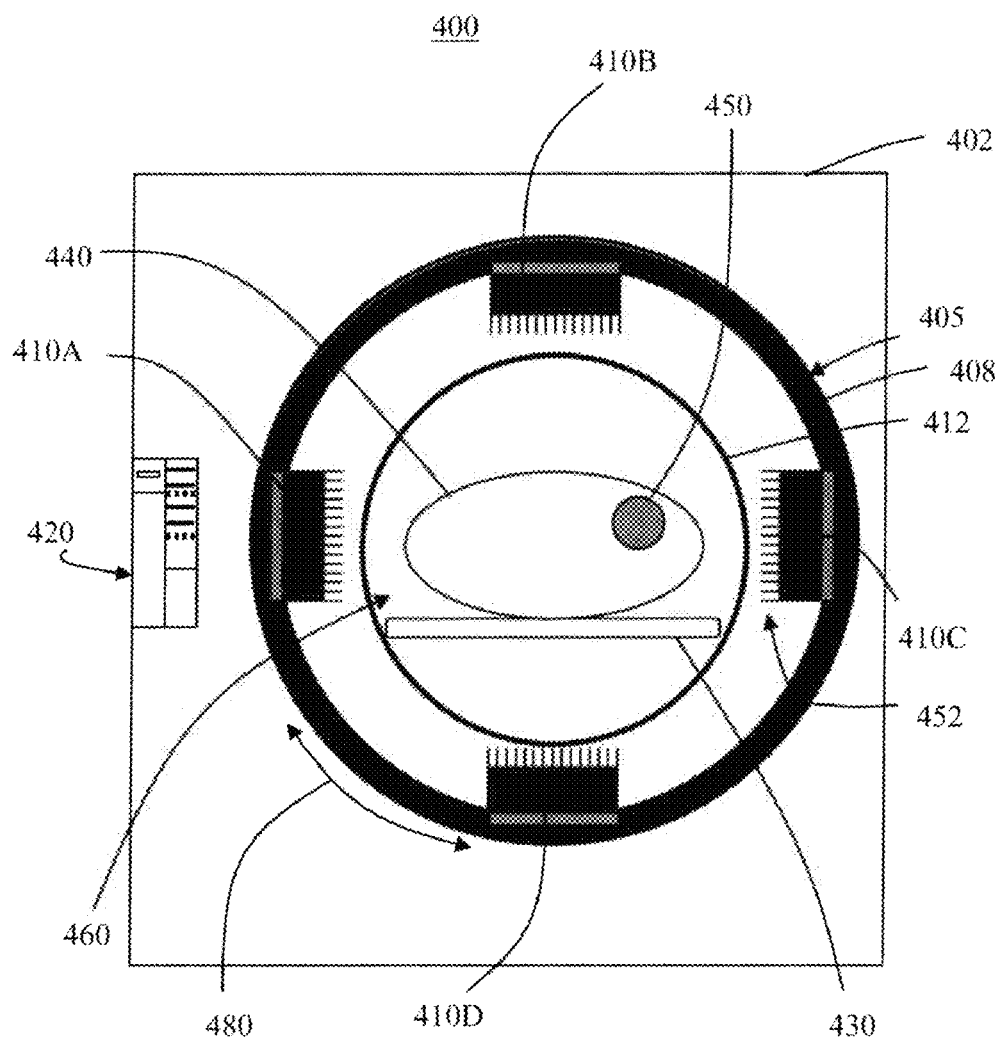
FIG. 4 is a schematic view of a SPECT system.

Referring to FIG. 4, a SPECT system 400 includes a stationary unit 402 and a rotating gantry ring 405. Gantry ring 405 provides an opening 460 for receiving a patient 440 positioned on a support table 430 within a cylindrical chamber. Gantry ring 405 carries nuclear imaging detectors 410A-D mounted to a common slip ring 408. A cover 412 of gantry ring 405 separates nuclear imaging detectors 410A-D from opening 460.

Figure 5:
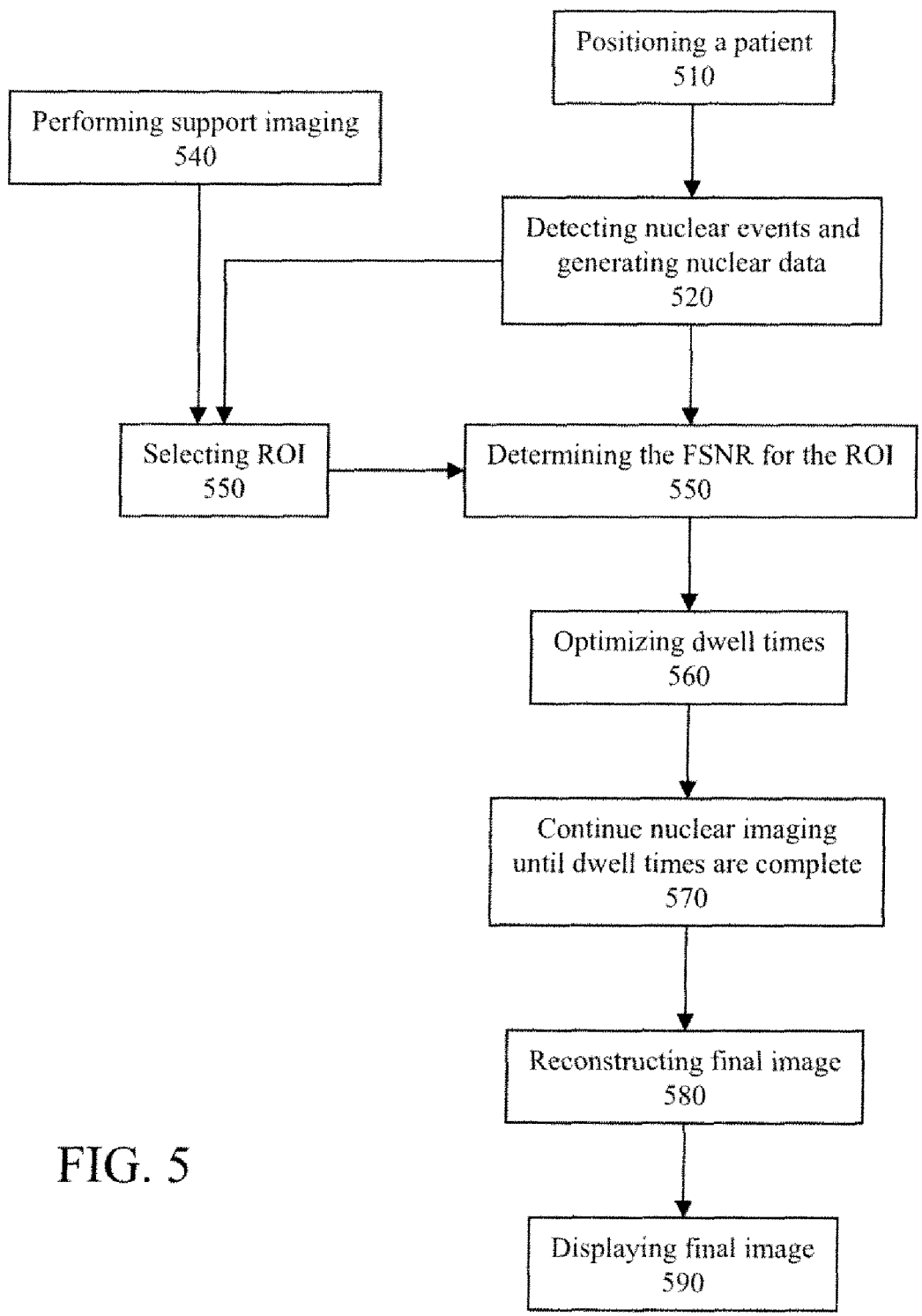
FIG. 5 is an example of a flow chart illustrating adaptation of dwell times.

In SPECT, nuclear imaging detectors usually include 1 to N detector heads rotating about the axis of the cylindrical chamber as indicated in FIG. 4 with a double-headed arrow 480. FIG. 5 shows four such detectors.

Each of nuclear imaging detectors 410A-D can be a solid state detector, such as a gamma camera that includes a direct converter and a collimator 452. Nuclear imaging detectors 410A-D and associated collimators 452 define a nuclear field-of-view (FOV). However, in general, various types of detectors and collimation schemes (e.g., active or passive, parallel, focusing, multi-focusing, or coded-aperture designs) can be used.

The stationary unit of SPECT system 400 can include, for example, a support table drive unit (not shown) and a control and reconstruction unit 420. Control and reconstruction unit 420 can control, for example, the position of patient table 430, the angular position of gantry ring 405, the speed of the rotation of gantry ring 405, the type of data acquisition with nuclear imaging detectors 410A-D, and the type of image reconstruction.

To acquire initial nuclear data, control and reconstruction unit 420 rotates gantry ring 408 around the patient either continuously or stepwise such that radiation emitted in a preset number of angular ranges is detected with nuclear imaging detectors 410A-D. Depending on whether SPECT system 400 uses a slip ring or cables to allow power to transfer to and nuclear data to transfer from nuclear imaging detectors 410A-D on rotating gantry ring 405 to the stationary unit, the revolutions of rotating gantry ring 405 are either unlimited or limited (to allow the gantry to unwind the cables).

For the image reconstruction of the nuclear data, control and reconstruction unit 420 can include a processor and memory having the reconstruction code thereon. The reconstruction techniques included in the code can take advantage, for example, of low SNR reconstruction as described, for example, in U.S. patent application Ser. No. 11/931,084, by H. Vija et al. entitled "EXTERNAL PIXON SMOOTHING FOR TOMOGRAPHIC IMAGE RECONSTRUCTION TECHNICAL FIELD," filed Oct. 31, 2007 and published as US 2009-0110254 A1 and U.S. patent application Ser. No. 11/931,195, by H. Vija et al. entitled "RECONSTRUCTING A TOMOGRAPHIC IMAGE," filed Oct. 31, 2007 and published as US 2009-0110255 A1. The code can further perform an analysis of statistical features (e.g., FSNR) of the initially detected nuclear data in a ROI 450 and thereby control the nuclear imaging process of SPECT system 400.

An example of operating a SPECT system with adapting dwell times is described in the following in connection with a flowchart 500 shown in FIG. 5. First, a patient is positioned on a support table and the radioactive substance is administered (step 510). Then, while the patient stays stationary on the support table, nuclear events of the administered substance cause the emission of radiation that is detected with nuclear imaging detectors in multiple viewing angles and provided in the form of nuclear data to a control and reconstruction unit (step 520).

From the nuclear data, one then reconstructs a rough nuclear image and selects a ROI (step 530). The quality of the nuclear image should allow one to distinguish a ROI from a surrounding region that is not of interest. This nuclear data can be the initial nuclear data of a longer nuclear imaging process, or nuclear data that originates from a separate pre-imaging process. Alternatively, a user can select the ROI based on an image derived from a separate imaging process (step 540). For example, one can select the ROI based on a previously generated CT image. In the latter case, the separately detected image needs to be registered in space to the field-of-view of the SPECT system 400.

Then, one determines a FSNR for the selected ROI (step 550) and improves a FSNR by varying the lengths of the dwell times for the various acquisition angles (step 560). The dwell times thus determined are expected to allow reconstruction of a nuclear image within a predefined FSNR. The initially detected nuclear data can also be analyzed to determine a required minimum acquisition time instead of, or in addition to adapting the dwell time.

In general, the determination of the minimum acquisition time and the dwell times can include analyzing the nuclear data with respect to a ROI and comparing an associated FSNR with a desired FSNR, modifying dwell times for individual viewing angles, and/or performing an optimization process of the minimum acquisition time and/or dwell times for improving the FSNR as described below. The determination of the adapted dwell times, in particular, calculating the FSNR, can also involve a system matrix that describes the performed imaging process for, e.g., SPECT reconstruction of a nuclear image.

The nuclear imaging process can then be continued or restarted so that for each viewing angle, at least for an amount of time that is as long as the determined dwell time for that viewing angle, nuclear data is acquired (step 570). For continuous rotation, the adapted dwell times can be realized by varying the rotation speed during a single rotation, while the measurement takes several rotations. For step-wise rotation, adapted dwell time can be realized by adjusting the lengths of the time intervals during which nuclear imaging detectors 410A-D are held in a particular angular position. In some embodiments, also the step-wise rotation performs several rotations. Using the adapted dwell times, SPECT system 400 is controlled in a manner that provides enough nuclear data to fulfill a preset FSNR within ROI 450.

Based on the nuclear data, one then reconstructs a final image (step 580). This reconstruction can involve the system matrix and use iteratively improved data modeling. The final image can then be displayed on a display or provided to a diagnostic analysis tool (step 590).

In the following, determining a minimum acquisition time and dwell times will be described in connection with a mathematical model.

Determining a Minimum Acquisition Time

In general, determining a minimum acquisition time is suitable for most planar and tomographic nuclear imaging types, including for example, SPECT and PET imaging. The determination of the minimum acquisition time can be based on the FSNR of a ROI, where the footprint consists of pixels of the nuclear 2D image in planar scintigraphy or of projected pixels of a volumetric image (voxels) in tomography (SPECT or PET) within the ROI. An evaluation of the FSNR in those pixels or voxels allows the system to adapt the minimum acquisition time to specific condition of the nuclear examination of a patient.

The minimum acquisition time can be determined by continuously accumulating and evaluating nuclear data until a desired FSNR is reached. Alternatively, one can determine the minimum acquisition time by using the initially determined count rate as a basis for estimating the minimum acquisition time required to reach a desired FSNR.

Determining Dwell Times

In SPECT imaging, the dwell time at different angles can similarly be adapted to improve the nuclear imaging process. If a SPECT scan is acquired in continuous rotation mode, the rate of rotation (speed profile) can be varied. If SPECT is performed in a step-and-shoot scan, the dwell time at each viewing angle can be varied. However, systems in which multiple detectors that are fixed in position with respect to each other to simultaneously collect data from various detection angles may have difficulty in adapting dwell times independently for those related detection angles.

In general, adaptation of dwell times (adaptive dwelling) can be achieved by analyzing the contributions of different viewing angles to the FSNR and modifying the dwell times of those viewing angles to increase (e.g., maximize) the FSNR for a fixed minimum acquisition time. Moreover, analyzing the FSNR allows adjusting the minimum acquisition time and the dwell time to requirements that are specifically adjusted to the patient and medical considerations.

In the following, an example of a mathematical description of adapting dwelling times $\{t_n\}$ is provided. Specifically, one adapts the dwell times $\{t_n\}$ of SPECT imaging based on the FSNR in a selected ROI, where n runs over the viewing angles of the detectors. At this point, a SPECT imaging mode is considered that uses a set of viewing angles in which the detectors are stationary ("point-and-stare" operation). This approach can be generalized to the continuous imaging mode, in which the detectors move without stopping, and the quantity to optimize is the angular velocity with which one or more detectors are rotated about the patient.

The use of variable dwell time suggests defining object emission in terms of emissivity per unit volume per unit time j (measured, say, in MBq cm$^{-3}$), instead of the conventional total emission during acquisition. The expected count detected at pixel i of viewing angle n then becomes $$m_i^{(n)} = t_n \sum_\alpha H_{i\alpha}^{(n)} j_\alpha$$

where $H^{(n)}$ is the system matrix for viewing angle n. When j is measured in MBq cm$^{-3}$ then $H^{(n)}$ includes the voxel volume.

In order to adapt the dwell times $\{t_n\}$, consider a simple estimate of the unnormalized emissivity given by the backward projection of the expected counts $$\hat{j}_\alpha = \sum_{ni} H_{i\alpha}^{(n)} m_i^{(n)} \qquad (1)$$

and sum it over a region of interest (ROI) defined by the voxel weights $\{w_\alpha\}$ $$\hat{J} = \sum_\alpha w_\alpha \hat{j}_\alpha = \sum_{ni\alpha} H_{i\alpha}^{(n)} w_\alpha m_i^{(n)} = \sum_{ni} \varphi_i^{(n)} m_i^{(n)}$$

where the $\{\varphi_i^{(n)}\}$ are the pixel weights of the ROI projected into the viewing angle n.

The optimized dwell times $\{t_n\}$ are determined by minimizing the relative variance of $\hat{J}$ $$\frac{V(\hat{J})}{E(\hat{J})^2} = \frac{\sum_{ni}(\varphi_i^{(n)})^2 m_i^{(n)}}{\left(\sum_{ni} \varphi_i^{(n)} m_i^{(n)}\right)^2} \qquad (2)$$

subject to a fixed acquisition time $$t = \sum_n t_n. \qquad (3)$$

By using the relative variance, one can avoid a dependence on the normalization of $\hat{J}$ and can use the un-normalized form that is adopted below.

For static emissions (dynamic and gated studies are discussed later), the count rates (counts per unit time) $\{\beta_i^{(n)}\}$ do not change significantly with time and can be estimated from a quick pre-scan or initial scanning period. The expected counts $\{m_i^{(n)}\}$ for each viewing angle n are then proportional to the dwell time $t_n$ to be determined $$m_i^{(n)} = t_n \beta_i^{(n)}$$

Taking the natural logarithm of Eq. (2) and adding a Larange multiplier (which turns out to be unity) to account for the constraint on available acquisition time, the merit function to minimize becomes $$\Lambda = \ln\left(\sum_n a_n t_n\right) - 2\ln\left(\sum_n b_n t_n\right) + \ln\left(\sum_n t_n\right) \quad (4)$$

where $$a_n = \sum_i (\varphi_i^n)^2 \beta_i^{(n)}$$

$$b_n = \sum_i \varphi_i^n \beta_i^{(n)}$$

Eq. (4) can be solved for the dwell times $\{t_n\}$ by standard nonlinear minimization schemes, starting with initial values that satisfy Eq. (3), for example, equal dwell times, and taking care not to change the sum of the dwell times during the iterative minimization.

A variant of the above scheme replaces Eq. (1) with $$\hat{j}_\alpha = \sum_{ni} t_n H_{i\alpha}^{(n)} m_i^{(n)}$$

The optimization proceeds analogously, with the merit function in Eq. (3) being replaced by $$\Lambda = \ln\left(\sum_n a_n t_n^3\right) - 2\ln\left(\sum_n b_n t_n^2\right) + \ln\left(\sum_n t_n\right) \quad (5)$$

The dwell times in the above mathematical description are "net" acquisition times and do not include the setup times required for each viewing angle.

Limiting the Viewing Angles

Tomographic reconstruction in medical applications often is based on noisy limited-angle tomographic data, e.g., based on viewing angles spanning less than 180° or, in general, less than that required by the uniqueness condition given in Orlov, "Theory of three dimensional reconstruction ii: the recovery operator," Soviet Phys. Crystallogr., 20, 429-433, 1976.

In general, the use of a reduced number of viewing angles, together with a reduction of associated overhead setup time, can decrease the minimum acquisition time.

Figure 6:
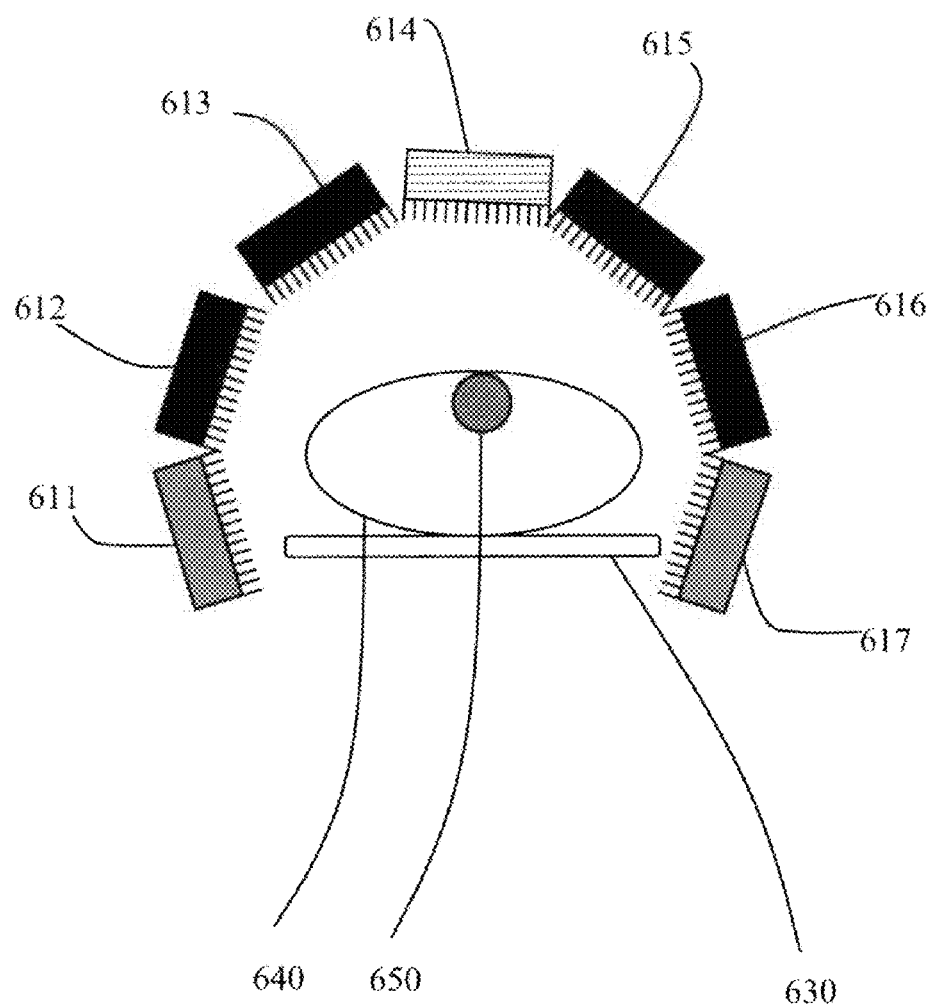
FIG. 6 is a schematic view illustrating limiting the number of viewing angles for SPECT imaging.

FIG. 6 shows a schematic drawing that illustrates a detector unit 610 that during SPECT imaging is kept stationary in several detector positions 611-617 corresponding to seven viewing angles that are used to image a patient 650 positioned on a support table 630. For simplicity of illustration, the number of detector positions has been limited to seven.

In a manner similar to that discussed in connection with adapting acquisition times, one can also statistically evaluate (e.g., via the FSNR for a ROI) image reconstruction and its dependence on the number of available viewing angles employed in a SPECT imaging process. One can then reduce the number of employed viewing angles and thereby distribute the available acquisition time among fewer viewing angles by selecting those viewing angles that contribute more to the FSNR. This procedure can be used to increase the quality of the nuclear image and/or reduce the amount of time required for achieving a desired FSNR in a ROI. In short, limiting the viewing angles can speed up and/or improve nuclear data acquisition by reducing the amount of time required for detecting the required nuclear data.

For limiting the number of viewing angles, more sophisticated image reconstruction methods can be employed, e.g., reconstruction methods based on the Pixon method, as described in the foregoing mentioned U.S. patent applications. Those reconstruction methods can contribute to a further reduction of viewing angles.

For example, the minimum complexity approach of the Pixon method, which restricts the ill-posed inversion problem, can support the reduction of viewing angles. The key idea thereby is that the minimum complexity approach restricts the realm of possible solutions to those that have the minimum complexity, and thereby obtains a better guess of the missing data.

Eliminating the shortest dwell time is done in an effort to ensure that the extra time thus available to the other viewing angles results in a smaller relative variance $V(\hat{J})/E(\hat{J})^2$ as discussed in the foregoing mathematical description of adaptive dwelling. If it does, the viewing angle in question can be eliminated. The process is then repeated until the elimination of a viewing angle turns out to be counterproductive, in which case that viewing angle is retained, and the elimination process is halted.

Referring again to FIG. 6, one can eliminate, for example, detector position 611 assuming that its contribution to the FSNR is small in view of the distance and angle of the detector to a ROI 650 of a patient 640. For the same reason, one may be able to eliminate detector position 617.

The acquisition time that is saved as a result of eliminating detector positions can then divided among remaining detector positions 612-616. This division need not be equal. For example, detector position 614, being the closest to ROI 650, could receive a smaller part than detector positions 612-613 and 616-617.

The foregoing proposed adaptation of the number of viewing angles does not rely on but can be used with a restoration of the missing data.

A number of embodiments of the invention have been described. Nevertheless, it will be understood that various modifications may be made without departing from the spirit and scope of the invention. For example, the adaptation of dwell times can be applied to various SPECT operation modes. For example, dwell-time adaptation can be applied to SPECT systems in which either the detectors or the collimators continuously rotate (e.g., SPRINT concepts), to spiral SPECT scanning modes, and to spatio-temporally consistent SPECT concepts.

While the control and reconstruction units were described to be configured for determining a minimum acquisition time or dwell time, the control and reconstruction units can additionally be configured to perform the final image reconstruction from the acquired nuclear data. However, in some systems, the final image reconstruction may be performed on a specialized external computer system.

The FSNR-based analysis can be performed with various image reconstruction methods. Examples include iterative image reconstruction methods, such as non-negative least square or Poisson-likelihood algorithms, that iteratively fit image models to the nuclear data. Such reconstruction methods can further use the Pixon method, which allows extracting information from data with a low signal-to-noise ratio. When determining the ROI based on an initial reconstruction, the reconstruction using the Pixon method can support the delineation of the ROI (e.g., when the signal of the ROI is determined) as well as the determination of the FSNR itself.

In some embodiments, the specific method by which the minimum acquisition time is determined is preordained in the operation protocol of the nuclear imaging system. In other embodiments, the specific method is selected on a case-by-case basis. However, the adapted amount of time (minimum acquisition time and/or dwell time) is determined adaptively based on acquired nuclear data. In some embodiments, one can perform an update of the minimum acquisition time and/or dwell time during the scanning process itself. List mode reconstruction can support real time adaptation. The update can be based on the acquired data itself or on test data that is repeatedly acquired during the scanning process.

In some nuclear imaging systems, nuclear data can be provided in a list mode in which the detected events are recorded with coordinates position r, detection time t, and energy E. The nuclear data can then be processed in real time using, for example, the Pixon method, as described, for example, in the foregoing identified U.S. Patent Applications. The scanning process can then continue during the processing of the first initially detected nuclear data.

For both adaptive dwelling and for adaptively limiting the viewing angles, physical boundary conditions can impose further constraints on the merit functions, e.g., the merit functions of Eqs. (4) and (5). As multiple detectors cannot be moved at will, the acquisition with those detectors may be synchronous, in which case those detectors have equal dwell times. Even with asynchronous acquisition, the minimum acquisition time is the same for all detectors. Those types of additional system-dependent constraints can be considered when optimizing the merit function.

Finally, dynamic and gated imaging require further consideration. In dynamic imaging, the assumption of constant count rates is not valid. In such cases, the count rates $\{\beta_i^{(m)}\}$ need to be reevaluated periodically during the acquisition, so that the adaptively determined dwell times can be adjusted accordingly. One way to reevaluate the count rates is to use the count rates measured in the previous time interval as the basis of adaptively selecting the dwell times for the next time interval.

In gated studies, the gates are much shorter than the dwell times. Consequently, it is not possible to change the dwell times for each acquisition. However, in such cases one can average the count rates of the gates. The specific weights used in this averaging can be designed to emphasize those gates having the higher diagnostic significance.

Accordingly, other embodiments are within the scope of the following claims.

What is claimed is:

1. A method of determining an acquisition time adapted to a region of interest for a nuclear imaging process of a patient, the method comprising:
   detecting radiation from at least a first viewing angle during a first test amount of time;
   generating first test data from the detected radiation;
   reconstructing a nuclear event distribution from the first test data;
   determining a test signal-to-noise ratio for the reconstructed nuclear event distribution within the region of interest; and
   determining the acquisition time using the test signal-to-noise ratio and the first test amount of time.

2. The method of claim 1, further comprising using the acquisition time as a control parameter for controlling the nuclear imaging process.

3. The method of claim 2, further comprising controlling the nuclear imaging process to acquire nuclear data during an amount of time at least as long as the acquisition time.

4. The method of claim 3, wherein the acquired nuclear data include the first test data.

5. The method of claim 3, further comprising reconstructing a nuclear image from the acquired nuclear data.

6. The method of claim 2, wherein the acquisition time is a dwell time associated with the detection of radiation from the first viewing angle, and wherein the method further comprises controlling the nuclear imaging process to acquire nuclear data from the first viewing angle during an amount of time at least as long as the dwell time.

7. The method of claim 6, wherein the acquired nuclear data includes the first test data.

8. The method of claim 6, wherein controlling the nuclear imaging process to acquire nuclear data from the first viewing angle includes controlling the speed of rotation of a detector to control an amount of time during which a detector can detect radiation emitted from the first viewing angle.

9. The method of claim 6, wherein controlling the nuclear imaging process to acquire nuclear data from the first viewing angle includes controlling an amount of time during which a detector is in a stationary position for detecting radiation from the first viewing angle.

10. The method of claim 1, wherein detecting radiation from at least a first viewing angle includes detecting radiation with a plurality of detector pixels of a detector.

11. The method of claim 10, wherein determining the test signal-to-noise ratio includes
   determining a count rate from the first test data and the first test amount of time and
   determining pixel weights associated with the detector pixels and the region of interest.

12. The method of claim 1, further comprising detecting radiation from at least in one additional viewing angle, and
   wherein determining the test signal-to-noise ratio for the region of interest includes determining count rates for the first viewing angle and the at least one additional viewing angle.

13. The method of claim 12, wherein determining the acquisition time includes determining dwell times for the first viewing angle and the at least one additional viewing angle by optimizing a merit function for the dwell times.

14. The method of claim 13, wherein the merit function is a function of at least one of a count rate for the first viewing angle, a count rate for the at least one additional viewing angle, and pixel weights associated with at least one of pixels of a detector system, the region of interest, the first viewing angle, and the at least one additional viewing angle.

15. The method of claim 1, further comprising providing a desired signal-to-noise ratio for the region of interest, and
   wherein determining the acquisition time includes determining that the test signal-to-noise ratio is at least as large as the desired signal-to-noise ratio.

16. A nuclear imaging apparatus comprising:
   a detector system configured to detect radiation during a nuclear imaging process from at least one viewing angle and to derive test data from the radiation; and
   a control and reconstruction unit configured to determine a test signal-to-noise ratio for a region of interest from the test data, and, based on the test signal-to-noise ratio, to control the amount of time of the nuclear imaging process during which the detector system is configured to detect radiation.

17. The nuclear imaging apparatus of claim 16, wherein the detector system includes at least one of a planar nuclear imaging detector, a SPECT detector, and a PET detector.

18. The nuclear imaging apparatus of claim 16, wherein the amount of time is a minimum acquisition time of the nuclear imaging process.

19. The nuclear imaging apparatus of claim 16, wherein the amount of time is a dwell time of a SPECT imaging process for the at least one viewing angle.

20. A non-transitory computer-readable medium having encoded thereon software for controlling a nuclear imaging system, the software including instructions for
   detecting radiation from at least a first viewing angle during a first amount of time;
   generating first test data from the detected radiation;
   reconstructing a nuclear event distribution from the first test data;
   determining a test signal-to-noise ratio for the reconstructed nuclear event distribution within the region of interest; and
   determining the acquisition time using the test signal-to-noise ratio and the first time interval.

* * * * *